(12) United States Patent
Patel et al.

(10) Patent No.: US 9,376,555 B2
(45) Date of Patent: *Jun. 28, 2016

(54) COLOR-CHANGING WOOD FILLER

(71) Applicant: Elmer's Products, Inc., Atlanta, GA (US)

(72) Inventors: Yogeshbhai Patel, Reynoldsburg, OH (US); Van R. Foster, Westerville, OH (US)

(73) Assignee: Elmer's Products, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/734,793

(22) Filed: Jun. 9, 2015

(65) Prior Publication Data

US 2015/0274946 A1  Oct. 1, 2015

Related U.S. Application Data

(63) Continuation-in-part of application No. 14/204,652, filed on Mar. 11, 2014, now Pat. No. 9,068,058, which is a continuation-in-part of application No. 13/832,989, filed on Mar. 15, 2013, now Pat. No. 8,927,620.

(51) Int. Cl.
*C08L 9/00* (2006.01)
*C08L 9/08* (2006.01)
*B27K 3/00* (2006.01)
*A61L 2/00* (2006.01)
*A61L 9/00* (2006.01)

(52) U.S. Cl.
CPC ... *C08L 9/08* (2013.01); *A61L 2/00* (2013.01); *A61L 9/00* (2013.01); *B27K 3/00* (2013.01)

(58) Field of Classification Search
CPC ............ C08K 7/28; C08K 5/32; C08K 5/466; C08L 5/1535
See application file for complete search history.

(56) References Cited

U.S. PATENT DOCUMENTS

| | | | |
|---|---|---|---|
| 3,660,324 A | 5/1972 | Onchi et al. | |
| 6,147,149 A | 11/2000 | Anderson et al. | |
| 6,512,027 B2 | 1/2003 | Kanai et al. | |
| 7,449,503 B2 | 11/2008 | Senturk | |
| 7,993,732 B2 | 8/2011 | Sasaki et al. | |
| 8,871,867 B2 | 10/2014 | Cheng et al. | |
| 2011/0021672 A1 | 1/2011 | Crews et al. | |

FOREIGN PATENT DOCUMENTS

| | | | |
|---|---|---|---|
| EP | 2452987 | 5/2012 | |
| WO | WO 2013/126377 | * 8/2013 | ................ C09J 4/00 |

OTHER PUBLICATIONS http://www.dow.com/en-US/markets-and-solutions/products/TRITON/TRITONX102#q=triton%20dispersant&t=All Cited as evidence only.(c) 1995.*
Trade sheet from OSHA from the Internet May 18, 2014 https://www.osha.gov/dts/chemicalsampling/data/CH_273993.html.

* cited by examiner

*Primary Examiner* — Nathan M Nutter
(74) *Attorney, Agent, or Firm* — Sutherland Asbill & Brennan LLP

(57) ABSTRACT

A composition for use as a wood-filter that includes a modified styrene butadiene latex; at least one pH indicator, wherein pH indicator causes the composition to change color as the composition dries; one or more types of microspheres, wherein the microspheres provide durability and stainability to the wood-filling composition; and high-density polyethylene fibers.

15 Claims, No Drawings

COLOR-CHANGING WOOD FILLER

This patent application is a continuation-in-part of U.S. patent application Ser. No. 14/204,652, filed on Mar. 11, 2014 and entitled "Color Changing Wood Filler", which was a continuation-in-part of U.S. patent application Ser. No. 13/832,989 filed on Mar. 15, 2013 and entitled "Color-Changing Wood Filling Composition", now U.S. Pat. No. 8,927,620, the disclosures of which are hereby incorporated by reference herein in their entirety and made part of the present U.S. utility patent application for all purposes.

BACKGROUND OF THE INVENTION

The described invention relates in general to compositions for repairing wood and similar surfaces, and more specifically to a wood-filling composition that includes a color-based indicator of dryness.

Current wood fillers are often tinted to match a particular color of a wood surface that requires repair or so the consumer may stain the repaired area to a desired color. However, current commercially available wood fillers do not provide the consumer with an accurate indicator of dryness so that sanding for eventual staining can be performed. Thus, in most cases, the consumer must wait for a predetermined period of time before sanding and staining or simply guess the appropriate time for such activity. Current wood fillers that utilize waterborne formulations technology are affected by relative humidity; thus, when evaluating the condition of such wood fillers, the end user is often left with the inability to know when to continue with the next repair step. Because an incorrect guess can result in an incomplete repair or unacceptable repair quality, there is an ongoing need for a wood-filling composition that includes an accurate visual indicator of dryness.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a first wood-filling composition is provided. This composition includes a styrene butadiene latex; at least one pH indicator, wherein the at least one pH indicator is operative to provide a visual indication that the composition is dry, and wherein the visual indication is based on a color change of the composition that occurs as the composition dries; microspheres, wherein the microspheres include glass or ceramic or both, and wherein the microspheres provide durability and stainability to the wood-filling composition; and at least one slump resister, wherein the at least one slump resister further includes high-density polyethylene fibers.

In accordance with another aspect of the present invention, a second wood-filling composition is provided. This composition consists of a styrene butadiene latex; at least one pH indicator, wherein the at least one pH indicator is operative to provide a visual indication that the composition is dry, and wherein the visual indication is based on a color change of the composition that occurs as the composition dries; microspheres, wherein the microspheres include glass or ceramic or both, and wherein the microspheres provide durability and stainability to the wood-filling composition; at least one slump resister, wherein the at least one slump resister further includes high-density polyethylene fibers; water; at least one pH controller; at least one surfactant; at least one dispersant; at least one freeze-thaw stabilizer; at least one bactericide; at least one defoamer; at least one thickener; at least one calcium carbonate filler; and at least one film former.

In yet another aspect of this invention, a third wood-filling composition is provided. This composition consists of a styrene butadiene latex; at least one pH indicator, wherein the at least one pH indicator is operative to provide a visual indication that the composition is dry, and wherein the visual indication is based on a color change of the composition that occurs as the composition dries; microspheres, wherein the microspheres include glass or ceramic or both, and wherein the microspheres provide durability and stainability to the wood-filling composition; a slump resister, wherein the slump resister further includes high-density polyethylene fibers, wherein the high-density polyethylene fibers have an average fiber length of about 0.1 mm, a fiber diameter of about 5 µm, and a surface area of about 12 m$^2$/gm; water; at least one pH controller; at least one surfactant; at least one dispersant; at least one freeze-thaw stabilizer; at least one bactericide; at least one defoamer; at least one thickener; at least one calcium carbonate filler; and at least one film former.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the associated descriptions are to be regarded as illustrative and not restrictive in nature.

DETAILED DESCRIPTION OF THE INVENTION

Exemplary embodiments of the present invention are described below. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present invention relates to a liquid or semi-solid wood-filling composition that includes a visual indicator of dryness following the application of the composition to a surface. This composition further includes one or more styrene butadiene rubber (SBR) polymers and glass or ceramic microspheres that provide superior product performance, primarily with regard to durability and stainability. The visual indicator is based on pH and when the wood filler of the present invention changes color (e.g., purple to white, magenta to beige, etc.) the repaired area is dry enough to be sanded and then painted, stained or otherwise processed without damage to or significant disruption of the wood filling composition.

A first exemplary formulation includes the following ingredients: water; a first pH controller that includes an amino alcohol such as AMP-95® manufactured by Angus Chemical Company (2-amino-2-methyl-1-propanol containing 5% water); a non-ionic surfactant such as Burco® APR-4007 manufactured by Burlington Chemical Co., LLC; a dispersant or anionic detergent polymer such as Burcosperse® AP Liquid manufactured by Burlington Chemical Co., LLC); a freeze-thaw stabilizer such as propylene glycol; a second pH controller such as potassium hydroxide (45% soln.); a SBR polymer such as the modified styrene butadiene latex Encor® DL 215 manufactured by Arkema, Inc.; a bactericide that includes aqueous blends of chlorinated and non-chlorinated isothiazolinones and 2-bromo-2-nitro-1,3-propanediol such as Acticide® LA manufactured by Thor, Inc.; a defoamer that includes insoluble oils, polydimethylsiloxanes and other silicones, alcohols, stearates and glycols or combinations thereof, such as Defoamer XZ manufactured by Nanjing Sixin Scientific and Technological Application Research institute Co., Ltd; a thickener that includes hydroxypropyl methylcellulose such as Methocel™ F4M manufactured by The Dow Chemical Company; a first calcium carbonate filler that includes dry ground marble such as Calwhite® manufactured by Imerys; a second calcium carbonate that includes dry ground calcium carbonate such as #10 White™ manufactured by Imerys; a first film-forming composition that includes a slow-evaporating glycol ether such as Dowanol DPnP manufactured by The Dow Chemical Company (dipropylene glycol n-propyl ether), a second film-forming composition that includes slow-evaporating, hydrophobic glycol ether such as Dowanol DPnB manufactured by The Dow Chemical Company (dipropylene glycol n-butyl ether); a pH indicator such as o-Cresolphthalein; and glass microspheres such as 3M™ Glass Bubbles K20 (density: 0.20 g/cc) manufactured by 3M Company. Example 1 (see below), includes these ingredients in specific percentages by weight. The formulation provided in Example 1 is referred to as Formula ZA55867 and changes from purple to white to indicate the appropriate time for sanding and staining or painting.

EXAMPLE 1

| Raw Material | % (by wt.) | Description |
|---|---|---|
| Water | 11.20 | — |
| AMP-95 ® | 0.30 | pH controller |
| Burco APR-4007 | 0.75 | surfactant/wetting agent |
| Burcosperse AP Liquid | 0.75 | dispersant |
| Propylene Glycol | 2.50 | freeze-thaw stabilizer |
| Potassium Hydroxide (45% soln.) | 0.25 | pH controller |
| Encor DL215 | 15.50 | SBR polymer |
| Acticide LA | 0.10 | bactericide |
| Defoamer XZ | 0.10 | defoamer |
| Methocel F4M | 0.45 | thickener |
| Calwhite | 41.15 | calcium carbonate filler |
| #10 White | 22.00 | calcium carbonate filler |
| Dowanol DPnP | 0.55 | film former |
| Dowanol DPnB | 0.30 | film former |
| o-Cresolphthalein | 0.10 | pH indicator |
| 3M Glass Bubbles K20 | 4.00 | glass microspheres |
|  | 100.00 |  |

A second exemplary formulation includes the following ingredients: water; a first pH controller that includes an amino alcohol such as AMP-95® manufactured by Angus Chemical Company (2-amino-2-methyl-1-propanol containing 5% water); a wetting agent such as Burco® APR-4007 manufactured by Burlington Chemical Co, a dispersant or anionic detergent polymer such as Burcosperse® AP Liquid manufactured by Burlington Chemical Co., LLC); a freeze-thaw stabilizer such as propylene glycol; a first colored pigment such as Joratint Umber 2TC; a second colored pigment such as Joratint Yellow TC; a second pH controller such as potassium hydroxide (45% soln.); a SBR polymer such as the modified styrene butadiene latex Encor® DL 215 latex manufactured by Arkema, Inc.; a bactericide that includes aqueous blends of chlorinated and non-chlorinated isothiazolinones and 2-bromo-2-nitro-1,3-propanediol such as Acticide® LA manufactured by Thor, Inc.; a defoamer that includes insoluble oils, polydimethylsiloxanes and other silicones, alcohols, stearates and glycols or combinations thereof, such as Defoamer XZ manufactured by Nanjing Sixin Scientific and Technological Application Research Institute Co., Ltd; a thickener that includes hydroxypropyl methylcellulose such as Methocel™ E4M manufactured by The Dow Chemical Company; include a first calcium carbonate filler that includes dry ground marble such as Calwhite® manufactured by Imerys; a second calcium carbonate that includes dry ground calcium carbonate such as #10 White™ manufactured by Imerys; a first film-forming composition that includes a slow-evaporating glycol ether such as Dowanol DPnP manufactured by The Dow Chemical Company (dipropylene glycol n-propyl ether), a second film-forming composition that includes slow-evaporating, hydrophobic glycol ether such as Dowanol DPnB manufactured by The Dow Chemical Company (dipropylene glycol n-butyl ether); a pH indicator such as o-Cresolphthalein; and glass microspheres such as 3M Glass Bubbles K20 (density: 0.20 g/cc) manufactured by 3M Company. Example 2 (see below), includes these ingredients in specific percentages by weight. The formulation provided in Example 2 is referred to as Formula ZA55868 and changes from magenta to beige to indicate the appropriate time for sanding and staining or painting.

EXAMPLE 2

| Raw Material | % (by wt.) | Description |
|---|---|---|
| Water | 11.20 | — |
| AMP-95 ® | 0.30 | pH controller |
| Burco APR-4007 | 0.75 | surfactant/wetting agent |
| Bureosperse AP Liquid | 0.75 | dispersant |
| Propylene Glycol | 2.50 | freeze-thaw stabilizer |
| Joratint Umber 2TC | 0.10 | color pigment |
| Joratint Yellow TC | 0.35 | color pigment |
| Potassium Hydroxide (45% soln.) | 0.25 | pH controller |
| Encor DL215 | 15.50 | SBR polymer |
| Acticide LA | 0.10 | bactericide |
| Defoamer XZ | 0.10 | defoamer |
| Methocel E4M | 0.45 | thickener |
| Calwhite | 40.68 | calcium carbonate filler |
| #10 White | 22.00 | calcium carbonate filler |
| Dowanol DPnP | 0.55 | film former |
| Dowanol DPnB | 0.30 | film former |
| o-Cresolphthalein | 0.12 | pH indicator |
| 3M Glass Bubbles K20 | 4.00 | glass microspheres |
|  | 100.00 |  |

A third exemplary formulation includes the following ingredients: water; a non-ionic surfactant such as Burco® APR-4007 manufactured by Burlington Chemical Co., LLC; a dispersant or anionic detergent polymer such as Burcosperse® AP Liquid manufactured by Burlington Chemical Co., LLC); a freeze-thaw stabilizer such as propylene glycol; a first pH controller that includes an amino alcohol such as AMP-95® manufactured by Angus Chemical Company (2-amino-2-methyl-1-propanol containing 5% water); a second pH controller such as potassium hydroxide (45% solution); Defoamer XZ manufactured by Nanjing Sixin Scientific and Technological Application Research Institute Co., Ltd; a calcium carbonate filler; a thickener that includes hydroxypropyl methylcellulose such as Methocel™ F4M manufactured by The Dow Chemical Company; a pH indicator such as o-Cresolphthalein; at least one slump resister that includes polyethylene ESS50F manufactured by MiniFI- BERS, Inc.; a SBR polymer such as the modified styrene butadiene latex Encor® DL 215 manufactured by Arkema, Inc.; a first film-forming composition that includes a slow-evaporating glycol ether such as Dowanol DPnP manufactured by The Dow Chemical Company (dipropylene glycol n-propyl ether); a second film-forming composition that includes slow-evaporating, hydrophobic glycol ether such as Dowanol DPnB manufactured by The Dow Chemical Company (dipropylene glycol n-butyl ether); a bactericide that includes aqueous blends of chlorinated and non-chlorinated isothiazolinones and 2-bromo-2-nitro-1,3-propanediol such as Acticide® LA manufactured by Thor, Inc.; and glass microspheres such as 3M™ Glass Bubbles K20 (density: 0.20 g/cc) manufactured by 3M Company. Example 3 (see below), includes these ingredients in specific percentages by weight. The formulation provided in Example 3 is referred to as Formula YP-5-6 and visibly changes color to indicate the appropriate time for sanding and staining or painting. The polyethylene ESS50F manufactured by MiniFIBERS, Inc provides adequate slump resistance for the formula. This material includes a fine grade of polyethylene fibers that serves as a replacement for wood flour or similar materials and is used to provide consistency and impart no-run properties to the formula. Wood flour is a known anti-sagging agent that is commonly used as an additive to prevent sagging (i.e., slump) in adhesives. Thus, a slump resister provides consistency, no-run properties, and prevents sagging of the formulation. More specifically, ESS50 includes high-density polyethylene (HDPE) fibers having an average fiber length of about 0.1 mm, a fiber diameter of about 5 μm, and a surface area of about 12 $m^2$/gm.

EXAMPLE 3

| Raw Material | % (by wt.) | Description |
| --- | --- | --- |
| Water | 32.50 | — |
| Burco APR-4007 | 0.50 | surfactant/wetting agent |
| Burcosperse AP Liquid | 0.50 | dispersant |
| Propylene glycol | 2.50 | freeze-thaw stabilizer |
| AMP-95 | 0.30 | pH controller |
| Potassium Hydroxide (45% soln.) | 0.25 | pH controller |
| Defoamer XZ | 0.20 | defoamer |
| Calcium carbonate | 14.50 | filler |
| Methocel F4M | 0.50 | thickener |
| o-Cresolphthalein | 0.10 | pH indicator |
| Mini Fibers ESS50F | 0.50 | slump resister |
| Encor DL-215 | 28.0 | SBR polymer |
| Dowanol DPnP | 1.00 | film former |
| Dowanol DPnB | 0.55 | film former |
| Acticide LA | 0.10 | bactericide |
| 3M Glass Bubbles K-20 | 18.00 | glass microspheres |
|  | 100.00 |  |

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. A composition for use as a wood-filler, consisting of:
   (a) a styrene butadiene latex;
   (b) at least one pH indicator, wherein the at least one pH indicator is operative to provide a visual indication that the composition is dry, and wherein the visual indication is based on a color change of the composition that occurs as the composition dries;
   (c) microspheres, wherein the microspheres comprise glass or ceramic or both, and wherein the microspheres provide durability and stainability to the composition;
   (d) at least one slump resister comprising high-density polyethylene fibers;
   (e) water;
   (f) at least one pH controller;
   (g) at least one surfactant;
   (h) at least one dispersant;
   (i) at least one freeze-thaw stabilizer;
   (j) at least one bactericide;
   (k) at least one defoamer;
   (l) at least one thickener;
   (m) at least one calcium carbonate filler; and
   (n) at least one film former.

2. The composition of claim 1, wherein the at least one freeze-thaw stabilizer includes propylene glycol; wherein the at least one bactericide includes an aqueous blend of chlorinated and non-chlorinated isothiazolinones and 2-bromo-2-nitro-1,3-propanediol; wherein the at least one thickener includes hydroxypropyl methylcellulose; wherein the at least one calcium carbonate filler includes dry ground calcium carbonate; and wherein the at least one film former contains dipropylene glycol n-propyl ether.

3. The composition of claim 1, wherein the at least one pH indicator is o-Cresolphthalein.

4. The composition of claim 1, wherein the high-density polyethylene fibers have an average fiber length of about 0.1 mm, a fiber diameter of about 5 μm, and a surface area of about 12 $m^2$/gm.

5. The composition of claim 1, wherein upon drying, the color of the composition changes from purple to white.

6. A composition for use as a wood-filler, consisting of:
   (a) a styrene butadiene latex;
   (b) at least one pH indicator, wherein the at least one pH indicator is operative to provide a visual indication that the composition is dry, and wherein the visual indication is based on a color change of the composition that occurs as the composition dries;
   (c) microspheres, wherein the microspheres include glass or ceramic or both, and wherein the microspheres provide durability and stainability to the composition;
   (d) a slump resister comprising high-density polyethylene fibers having an average fiber length of about 0.1 mm, a fiber diameter of about 5 μm, and a surface area of about 12 $m^2$/gm;
   (e) water;
   (f) at least one pH controller;
   (g) at least one surfactant;
   (h) at least one dispersant;
   (i) at least one freeze-thaw stabilizer;
   (j) at least one bactericide;
   (k) at least one defoamer;
   (l) at least one thickener;
   (m) at least one calcium carbonate filler; and
   (n) at least one film former.

7. The composition of claim 6, wherein the at least one freeze-thaw stabilizer includes propylene glycol; wherein the at least one bactericide includes an aqueous blend of chlorinated and non-chlorinated isothiazolinones and 2-bromo-2-nitro-1,3-propanediol; wherein the at least one thickener includes hydroxypropyl methylcellulose; wherein the at least one calcium carbonate filler includes dry ground calcium carbonate; and wherein the at least one film former contains dipropylene glycol n-propyl ether.

8. The composition of claim 1, wherein the at least one pH indicator is o-Cresolphthalein.

9. The composition of claim 1, wherein upon drying, the color of the composition changes from purple to white.

10. A wood-filler composition, consisting of:
 (a) a styrene butadiene latex;
 (b) at least one pH indicator, wherein the at least one pH indicator is operative to provide a visual indication that the composition is dry, and wherein the visual indication is based on a color change of the composition that occurs as the composition dries;
 (c) microspheres, wherein the microspheres comprise glass or ceramic or both, and wherein the microspheres provide durability and stainability to the wood-filler composition;
 (d) a slump resister;
 (e) water;
 (f) at least one pH controller;
 (g) at least one surfactant;
 (h) at least one dispersant;
 (i) at least one freeze-thaw stabilizer;
 (j) at least one bactericide;
 (k) at least one defoamer;
 (l) at least one thickener;
 (m) at least one calcium carbonate filler; and
 (n) at least one film former.

11. The composition of claim 10, wherein the slump resister comprises high-density polyethylene fibers.

12. The composition of claim 11, wherein the high-density polyethylene fibers have an average fiber length of about 0.1 mm, a fiber diameter of about 5 μm, and a surface area of about 12 $m^2/gm$.

13. The composition of claim 10, wherein the at least one freeze-thaw stabilizer includes propylene glycol; wherein the at least one bactericide includes an aqueous blend of chlorinated and non-chlorinated isothiazolinones and 2-bromo-2-nitro-1,3-propanediol; wherein the at least one thickener includes hydroxypropyl methylcellulose; wherein the at least one calcium carbonate filler includes dry ground calcium carbonate; and wherein the at least one film former contains dipropylene glycol n-propyl ether.

14. The composition of claim 10, wherein the at least one pH indicator is o-Cresolphthalein.

15. The composition of claim 10, wherein upon drying, the color of the composition changes from purple to white.

\* \* \* \* \*